United States Patent [19]
Goffman et al.

[11] Patent Number: 4,789,445
[45] Date of Patent: Dec. 6, 1988

[54] METHOD FOR THE ELECTRODEPOSITION OF METALS

[75] Inventors: Martin Goffman, Edison; Val Kudryk, Closter, both of N.J.

[73] Assignee: ASARCO Incorporated, New York, N.Y.

[21] Appl. No.: 933,284

[22] Filed: Nov. 19, 1986

Related U.S. Application Data

[63] Continuation of Ser. No. 495,312, May 16, 1983.

[51] Int. Cl.$^4$ .................. C25C 1/16; G01N 27/26
[52] U.S. Cl. ................................. 204/114; 204/434
[58] Field of Search .................. 204/1 T, 55 R, 55 Y, 204/114, 118, 130, 434

[56] References Cited

U.S. PATENT DOCUMENTS

| | | | |
|---|---|---|---|
| 3,073,757 | 1/1963 | Ladisch | 204/1 T |
| 3,649,180 | 3/1972 | McKay et al. | 204/114 |
| 3,755,098 | 8/1973 | Major et al. | 204/55 R |
| 4,013,412 | 3/1977 | Mukae | 204/1 T |
| 4,146,437 | 3/1979 | O'Keefe | 204/1 T |
| 4,153,521 | 5/1979 | Litvak et al. | 204/1 T |
| 4,217,189 | 8/1980 | Kerby | 204/1 T |
| 4,324,621 | 4/1982 | Kerby | 204/1 T |

*Primary Examiner*—Donald R. Valentine
*Attorney, Agent, or Firm*—John J. Tomaszewski; Kenneth A. Koch

[57] ABSTRACT

The invention relates to an improved electrodeposition process for the recovery of metals by controlling the concentration of certain impurities in the electrolyte. For a zinc sulfate electrolyte, control of only the antimony impurity level below a predetermined value provides an efficient electrodeposition process.

8 Claims, 2 Drawing Sheets

METHOD FOR THE ELECTRODEPOSITION OF METALS

This is a continutation of co-pending application Ser. No. 495,312 filed on May 16, 1983 now abandoned.

BACKGROUND OF THE INVENTION

This invention relates to a method for the electrodeposition of metals, and, more particularly, to a method for continuously measuring and adjusting the concentration of very low levels of impurities, particularly antimony impurities, in electrolyte solutions, particularly zinc electrolyte, during electrolytic metal recovery operations.

In processes involving the electrodeposition of metals such as electrowinning, electrorefining and electroplating, electrolytic solutions are used which contain impurites that when present above certain predetermined concentrations can electrodeposit with the plated metal and thereby either contaminate or cause resolution of the deposit, with a corresponding decrease in the efficiency of the metal deposition process. Consequently, an effective technique for monitoring the purity of the electrolyte supplied to and used in the electrolysis section of the metal plant is required since the current efficiency is greatly affected by the presence of even minute quantities of undesirable impurity metal ions.

In modern industrial operations, metals such as zinc are produced from ores and/or concentrates by either roasting and leaching, or direct leaching so as to generate a solution, e.g., zinc sulfate, which contains a substantial amount and number of impurities. The solution is then purified by conventional techniques, thereby lowering the deleterious impurities to levels which will not interfere with the zinc recovery process. More particularly, when impurities such as antimony, arsenic, cadmium, cobalt, copper, germanium, nickel, selenium and tellurium are present above certain concentrations in various electrolyte solutions, ranging from 0.01 ppm (parts per million) for antimony to 2.0 ppm for cadmium in the case of zinc electrolyte, the hydrogen overpotential on zinc can be reduced, thus significantly impairing current efficiency while also permitting the dissolving of already deposited pure zinc metal.

The art has made many attempts to solve this troublesome problem, the most common being the use of analytical techniques for determining the concentration of the various impurities. However, such processes have all proven unsatisfactory due to the lengthy and unreliable techniques available for measuring the low levels of impurities found in the electrolyte. Additionally, these technique are deficient for a process control method since the variables to be monitored can frequently change significantly between the time the measurement is taken and the time the sample is quantitatively analyzed. The addition of organic reagents such as animal glue can inhibit the deleterious effects, but are frequently effective only within certain relatively narrow impurity ranges.

The importance of determining the quality of zinc electrolyte is reflected in the number of published references discussing the problem, and the number of different techniques investigated, none of which have gained wide acceptance in the zinc industry. One such technique, reported by R. C. Kerby et all. "The Construction and Operation of a Meter for Measuring the Quality of Zinc Electrolytes", Technical Bulletin TB 160, Dept. of Canadian Energy, Mines and Resources, September 1972, measures the evolution of hydrogen gas in a small cell as a measure of current efficiency. However, this only provides a qualitative indirect measurement and can be influenced by factors other than impurity levels. In U.S. Pat. Nos. 4,324,621 and 4,217,189, R. C. Kerby discusses many attempts to measure and/or determine the effects of impurities and discloses methods for measuring the activation overpotential between the cathode and a reference cell, and relates this to the concentration of impurities and polarizing affecting agents present in the sample. The processes for the purification of electrolyte and the electrodeposition of metals are subsequently adjusted in relation to the earlier measured value. A method for measuring the amount of current required to plate and then deplate, which can be related to the electrolyte quality, is disclosed by A. D'Este et al. in "Montevecchio" 16, Nos. 3-4, 1-11 (1965). A report by R. V. Wong of EG&G Princeton Applied Research entitled "Electrochemical Techniques for the Analysis of Plating Baths" discusses the use of differential pulse polarography to analyze major and minor constituents in a plating bath.

It is an object of this invention to provide a new and improved method for the electrodeposition of metals.

Another object is to provide a method for analyzing low levels of impurities, e.g., in electroplating solutions, by using a polarograph.

Other objects will be apparent from the following description.

SUMMARY OF THE INVENTION

Broadly, the invention discloses a method for the electrodeposition, usually by electrowinning, of a metal, selected from the group of zinc, copper, lead, iron, cobalt, nickel, manganese, chromium, tin, cadmium, bismuth, indium, silver, gold, rhodium, ano platinium; and most preferably, zinc. The metal to be electrodeposited frequently contains a significant amount of at least one of a plurality of various impurities selected from the group of antimony, arsenic, cadmium, cobalt, copper, germanium, nickel, selenium and tellurium. Depending on the metal to be plated, each electrolyte has impurities having predetermined concentrations that range, for zinc sulfate, from about 0.01 ppm, e.g., 0.02 ppm, for antimony to about 2.0 ppm for cadmium, and which should be continually kept below its predetermined concentration to achieve an efficient electroplating process. The method involves periodically preferably very frequently, sampling a sufficient, i.e., measurable amount of electrolyte solution, and promptly determining the concentration level of at least one such impurity, and particularly antimony in the recovery of zinc, by means of an effective analytical technique, preferably a polarographic technique, using a hanging drop mercury electrode method, to accurately determine the sought after impurity concentrations. Upon the completion of measuring, the concentration of the desired impurity is calculated, preferably by a high speed calculating means, and most preferably by a microcomputer, whereby the electrolyte impurity concentration can be promptly readjusted to a desired value below the predetermined impurity concentration. This process control analysis is continually repeated for the duration of the electrodeposition process.

DETAILED DESCRIPTION

Figure 1:
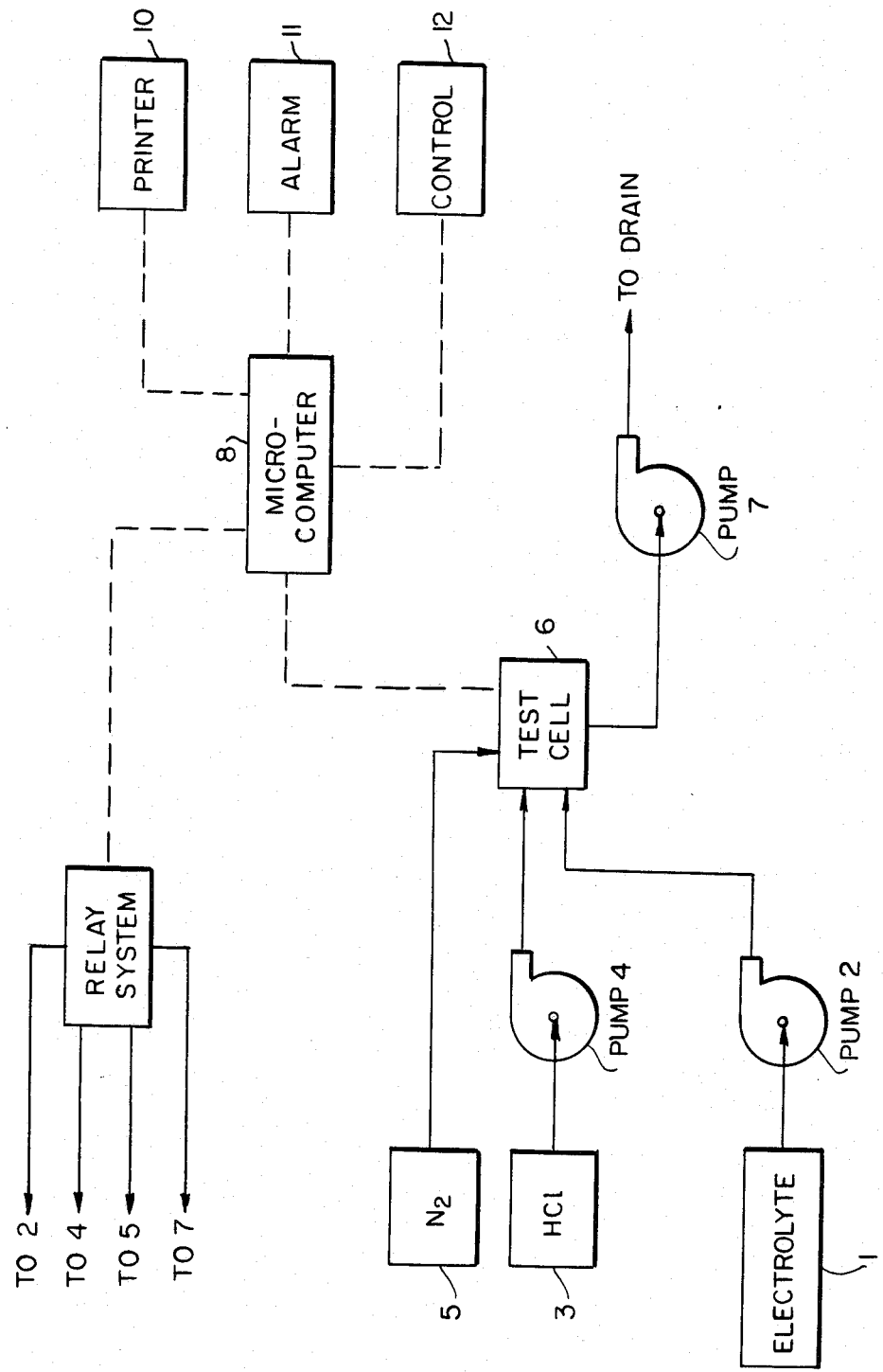
FIG. 1 outlines a schematic diagram of the preferred process of the invention.

Viewing FIG. 1, a schematic outline of the preferred process control system is set forth. Unit 1 represents any suitable source of an electrolyte solution, for example, a zinc sulfate container in the common case of recovering zinc in an electrowinning operation, such as an industrial electrorefining tankhouse. Pump 2 withdraws a measurable sample of the zinc sulfate solution from source 1 and transports it to polarograph cell 6, or, in the broadest embodiment of the invention, any suitable measuring means including spectrographic techniques as atomic absorption, ultraviolet absorption and inductively coupled plasma, together with specific ion and cyclic voltammetry techniques which can quickly and accurately determine the low concentration of impurities contained therein. Hydrochloric acid, which is stored in tank 3, is concurrently supplied to the polarograph cell 6 by pump 4, while nitrogen gas, stored in tank 5, is bubbled through the electrolyte sample in order to displace any dissolved oxygen present. The polarographic measurement of the particular impurity concentration to be determined is then made in test cell 6, preferably by using a hanging drop mercury electrode. After the impurity level has been measured, the cell can be emptied to drain by pump 7, and the cycle then repeated for a determination either on a new sample, or, the measurement can be repeated on the present sample to ensure its accuracy.

Figure 3:
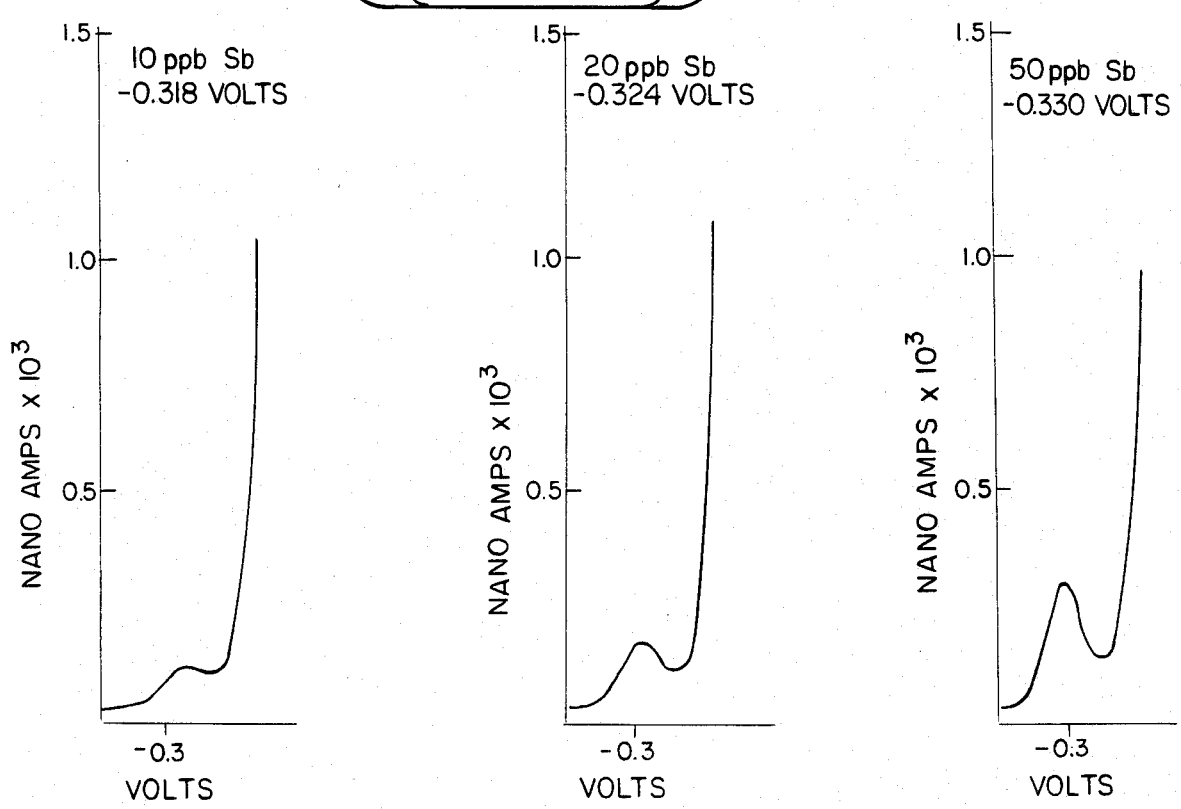
FIG. 3 is a differential pulse polarogram for a sample of zinc sulfate electrolyte showing the concentration of antimony as a function of the peak height.

Upon completion of the measurement, the current and potential data are delivered to, in the broadest embodiment of the invention, an effective high speed computing means, which in the preferred embodiment is a state of the art electronic computer, and most preferably, a microcomputer 8. Microcomputer 8 is programmed the art programming techniques, and preferably programmed so as to record a polarographic or, other suitable data containing curve as shown in FIG. 3 and/or calculate the impurity concentration and exhibit the result on a screen or be printed out by printer 10 or the like. The microcomputer is preferably programmed to activate the measuring system in a predetermined desired sequence so as to effectively operate pumps 2, 4 and 7 and nitrogren addition 5, together with automatically starting and assisting in the polarographic analysis; as well as having an indicator means in alarm 11 and control unit 12 when the impurity concentration rises above a programmed value corresponding to the particular impurity concentration and which when activated, can, for example, divert the flow of electrolyte to a storage tank for corrective action.

The computing means can be programmed for substantially continuous monitoring, by, for example, programming the data pertaining to cycle sequence and timing for each operation. The computer is particularly useful in properly activating the dropping mercury electrode to generate a fresh mercury drop at the electrode for each preferred polarographic determination. The potential value is held for a predetermined time at a predetermined value in order to electrolyze the impurity to be determined. After a predetermined time, the potential is then reversed and the voltage and current data collected by the computer.

An important element of the process as pertains to zinc solutions is the surprising discovery that reducing the antimony content below its desired limit, e.g., 0.02 ppm, provides a solution which may be electrolytically refined with high efficiency. More specifically, it was discovered that when the antimony concentration is below about 0.02 ppm in a zinc sulfate solution, all other deleterious impurity concentrations were discovered to be below levels that would be harmful to the electrodeposition process. This relationship can be seen more clearly in Table I, where an impurity analysis of zinc sulfate electrolyte solutions is presented.

TABLE I

| Test | Impurity Analysis (ppm) | | | | | | |
|---|---|---|---|---|---|---|---|
|  | Sb | Co | Cu | Cd | Ge | Ni | As |
| 1 | 1.8 | 0.80 | 2.0 | 19.0 | 0.15 | 0.1 | 0.02 |
| 2 | 0.44 | 0.50 | 1.0 | 3.0 | 0.02 | 0.1 | 0.01 |
| 3 | 0.41 | 0.10 | 2.0 | 12.0 | 0.10 | 0.05 | 0.01 |
| 4 | 0.29 | 0.30 | 0.4 | 2.0 | 0.01 | 0.05 | 0.01 |
| 5 | 0.11 | 0.30 | 0.4 | 1.0 | <0.005 | <0.05 | <0.01 |
| 6 | 0.02 | 0.1 | <0.4 | 2.0 | <0.005 | <0.05 | <0.01 |
| 7 | 0.01 | 0.2 | <0.4 | 1.0 | <0.005 | <0.05 | <0.01 |
| 8 | 0.01 | 0.2 | <0.4 | 2.0 | <0.005 | <0.05 | <0.01 |
| 9 | 0.008 | 0.3 | <0.4 | 0.5 | <0.005 | <0.05 | <0.01 |

As is shown in Table 1 lowering of the antimony concentration below certain levels in the zinc sulfate electrolyte also surprisingly reduces the impurity levels of the other harmful elements below their deleterious levels, as well. This development makes it unnecessary to analyze for impurities other than antimony in the case of the zinc electrodeposition processes, thus both greatly simplifying the purity analysis and also greatly reducing the time necessary to complete the analysis. Preferred methods for treating the zinc sulfate electrolyte to lower the antimony impurity levels are well known in the industry and commonly the solution is contacted with zinc dust. In a zinc electrodeposition process the limit for some of the impurities is approximately as follows (ppm): cobalt-0.3; copper-0.5: cadmium-2; germanium-<005; nickel-<.0.1; and arsenic-<0.1.

Figure 2:
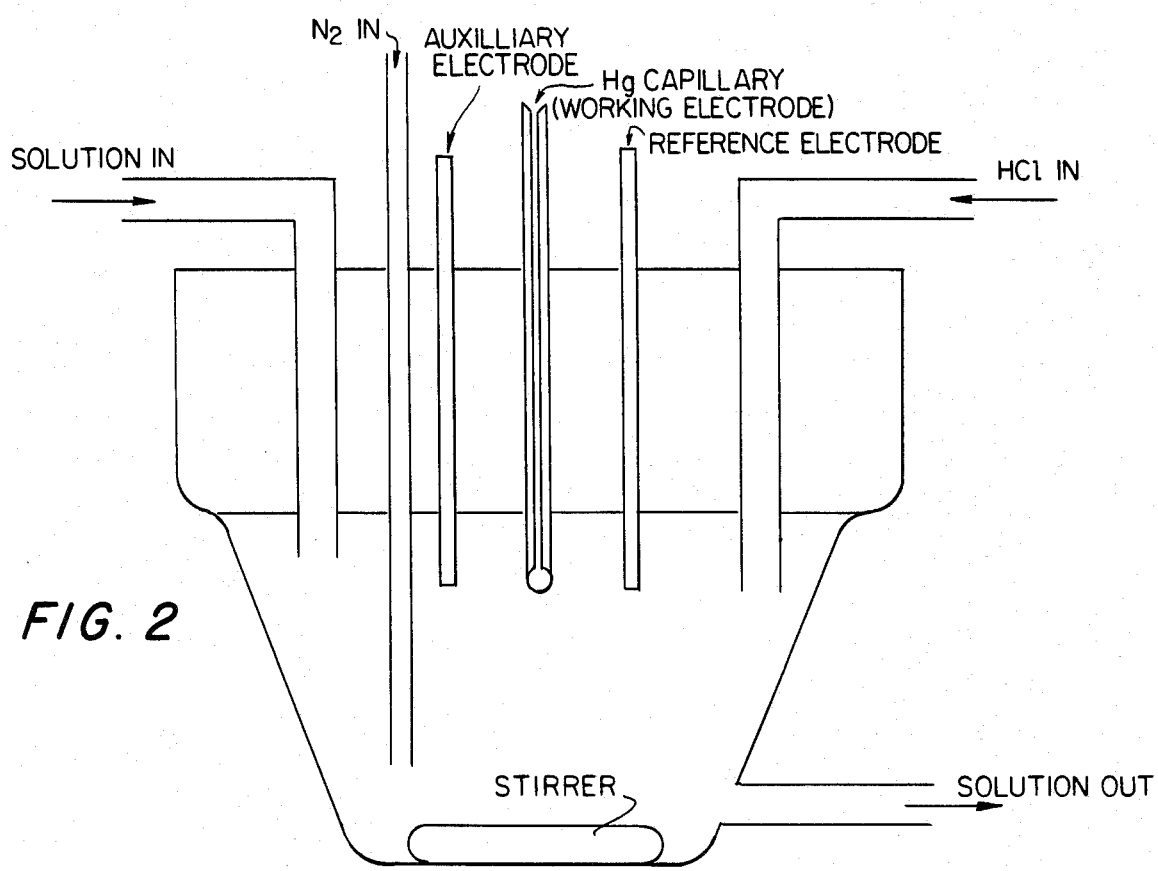
FIG. 2 shows an electrode test cell for a polarograph.

Since the preferred polarographic analysis for antimony is usually conducted on solutions extremely low in impurities, i.e., less than 0.02 ppm antimony, it is important to use a specialized procedure which is a preferred embodiment of the invention, to accurately measure these low concentrations since the polarograph is normally an instrument incapable of consistently providing accurate measurements at these low concentrations. We have found that using differential pulse polarography whereby the mercury at the tip of the electrode is not continuously dropped, but instead kept in a hanging mode for about 60 to 180 seconds, e.g., 120 seconds, and at a fixed voltage that varies depending on the particular impurity in question, was effective. The polarity is then altered, the impurity deplated and potential-current data gathered. The voltage scan range for antimony is about −0.420 to −0.150 volts, with the peak occurring at approximately −0.32 volts. FIG. 2 shows a typical polarographic test cell and FIG. 3 a typical differential pulse polarogram for antimony analysis by this technique.

As can be seen from FIG. 3, the antimony concentration is determined by measuring the peak height after suitable calibration to standardize the technique as well known to those skilled in the art. Such techniques and other information relating to polarography and differential pulse polarography may be found in "Polarographic Techniques", 2nd Edition, by L. Meites, Interscience, NYC, 1965 and in "Modern Polarographic Methods in Analytical Chemistry" by A. M. Bond Marcel Dekker, Inc., 1980, both publications being hereby incorporated by reference.

Due to the very low concentrations of impurities in the presence of a relatively high concentration of zinc, or, in the broadest embodiment of the invention, metal ions which are desired to be electrodeposited, it is preferable to include complexing agents in order to shift the ion deposition potential. In the determination of antimony levels it is important to add sufficient HCl to the solution so as to create about a 1 to 12, e.g., 8, normal acid solution. For the determination of cadmium in zinc solutions, however, citric acid is added to produce about a 0.125 molar solution As will be apparent to those skilled in the art, different complexing agents at varying amounts as well as different mercury hanging times and voltages determined by routine experimentation may be necessary depending on the metal ion and electrolyte to be analyzed.

The preferred operating temperature with the polarograph is about room temperature, in the range of 25-35° C., although the electrodeposition processes can be conducted at other temperatures if so desired. In the room temperature range, it has been found that temperature variations were not a significant variable.

The accuracy of polarographic analysis for zinc sulfate solutions using the preferred techniques described above is reflected in Table II in the comparison of data on the identical solutions when analyzed by standard atomic absorption (AA) techniques and polarography.

TABLE II

| Sample No. | Antimony (ppm) | |
|---|---|---|
| | AA Analysis | Polarographic |
| 1 | 0.100 | 0.100 |
| 2 | 0.050 | 0.046 |
| 3 | 0.050 | 0.052 |
| 4 | 0.036 | 0.034 |
| 5 | 0.035 | 0.039 |
| 6 | 0.030 | 0.029 |
| 7 | 0.020 | 0.019 |
| 8 | 0.011 | 0.010 |
| 9 | 0.010 | 0.010 |
| 10 | 0.010 | 0.009 |

TABLE II-continued

| Sample No. | Antimony (ppm) | |
|---|---|---|
| | AA Analysis | Polarographic |
| 11 | 0.010 | 0.010 |

It is to be understood that although the examples are specific to zinc sulfate and the zinc sulfate-antimony solutions, the principles of the invention also apply to all other systems containing similar electrolytes and having similar voltage impairing impurities.

We claim:

1. A method for the electrodeposition of zinc containing a measurable concentration of a plurality of impurities including antimony in its electrolyte solution wherein the concentrations of the impurities are maintained below deleterious levels by the control of only the antimony impurity concentration, said method characterized by the following steps
   sampling a sufficient amount of electrolyte from the electrolyte solution;
   measuring the concentration level of antimony impurity
   in the electrolyte sample by means of an effective measuring technique;
   readjusting the antimony impurity level of the electrolyte solution below 0.02 ppm by the addition of zinc dust to the electrolyte;
   continually repeating at predetermined intervals the above sequence of steps throughout the duration of the electrodeposition process.

2. A method as claimed in claim 1 wherein the electrodeposition process is the electrowinning of zinc.

3. A method as claimed in claim 1 wherein the effective measuring technique is selected from the group of polarography, atomic absorption, ultra violet absorption, inductively coupled plasma, specific ion and cyclic voltammetry techniques.

4. A method as claimed in claim 3 wherein the measuring technique is differential pulse polarography.

5. A method as claimed in claim 4 wherein the polarographic technique involves using a hanging drop mercury electrode capable of detecting antimony levels as low as 0.010 ppm.

6. A method as claimed in claim 1 where the readjusting of the impurity level of the electrolyte solution is made by an effective computing means.

7. The method as claimed in claim 6 wherein the computing means is a microcomputer.

8. A method as claimed in claim 1 wherein the electrolyte solution to be sampled is an aqueous solution of zinc sulfate.

* * * * *